US009709587B2

United States Patent
Hagiwara et al.

(10) Patent No.: US 9,709,587 B2
(45) Date of Patent: Jul. 18, 2017

(54) AUTOMATIC ANALYZER AND REAGENT PROCESSING METHOD IN AUTOMATIC ANALYZER

(71) Applicant: HITACHI HIGH-TECHNOLOGIES CORPORATION, Tokyo (JP)

(72) Inventors: Takaaki Hagiwara, Tokyo (JP); Kazunori Yamazawa, Tokyo (JP); Hiroki Fujita, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 3 days.

(21) Appl. No.: 14/370,076

(22) PCT Filed: Dec. 26, 2012

(86) PCT No.: PCT/JP2012/083745
§ 371 (c)(1),
(2) Date: Jul. 1, 2014

(87) PCT Pub. No.: WO2013/103119
PCT Pub. Date: Jul. 11, 2013

(65) Prior Publication Data
US 2014/0356233 A1 Dec. 4, 2014

(30) Foreign Application Priority Data
Jan. 5, 2012 (JP) ................................ 2012-000837

(51) Int. Cl.
*G01N 35/00* (2006.01)
*B01J 19/00* (2006.01)
(Continued)

(52) U.S. Cl.
CPC ..... *G01N 35/1016* (2013.01); *G01N 35/0092* (2013.01); *G01N 35/00693* (2013.01);
(Continued)

(58) Field of Classification Search
CPC ....... G01N 2035/0094; G01N 35/0092; G01N 35/00693
See application file for complete search history.

(56) References Cited

U.S. PATENT DOCUMENTS 6,090,630 A 7/2000 Koakutsu et al.
2004/0253146 A1* 12/2004 Shiba et al. .................... 422/64
(Continued)

FOREIGN PATENT DOCUMENTS

JP 09-043244 A 2/1997
JP 10-142230 A 5/1998
(Continued)

OTHER PUBLICATIONS

International Preliminary Report on Patentability received in International Application No. PCT/JP2012/083745 dated Jul. 17, 2014.

*Primary Examiner* — P. Kathryn Wright
(74) *Attorney, Agent, or Firm* — Mattingly & Malur, PC (57) ABSTRACT

An automatic analyzer is capable of performing a preparation process on a reagent used to measure a highly urgent test item even during analysis operation, and is configured as follows. If there is no parameter for the analysis item regarding a new reagent, the parameters are downloaded. If the priority of reagent preparation is "high," a sample pipetting scheduling process is temporarily stopped. If the priority of reagent preparation is not "high," it is determined whether a waiting time limit has been exceeded, and if it has, the sample pipetting scheduling process is stopped temporarily, reagent preparation scheduling is performed, and the sample pipetting scheduling process is resumed. If it is determined that the waiting time limit has not been exceeded, if the priority of reagent preparation is "medium," and if the reagent preparation mechanism is found available, then reagent preparation scheduling is performed.

9 Claims, 8 Drawing Sheets (51) Int. Cl.
*G01N 35/10* (2006.01)
*G01N 35/04* (2006.01)

(52) U.S. Cl.
CPC .............. *G01N 35/1002* (2013.01); *G01N 2035/00673* (2013.01); *G01N 2035/0443* (2013.01); *G01N 2035/0444* (2013.01)

(56) References Cited

U.S. PATENT DOCUMENTS

| | | | |
|---|---|---|---|
| 2005/0175506 A1* | 8/2005 | Matsubara | G01N 35/00712 422/68.1 |
| 2008/0240991 A1* | 10/2008 | Wakamiya et al. | 422/68.1 |
| 2008/0241937 A1* | 10/2008 | Wakamiya | G01N 35/00693 436/43 |
| 2009/0281930 A1* | 11/2009 | Sakagami | 705/28 |
| 2012/0294762 A1* | 11/2012 | Frank et al. | 422/63 |

FOREIGN PATENT DOCUMENTS

| | | |
|---|---|---|
| JP | 2004-340649 A | 12/2004 |
| JP | 2006-337386 A | 12/2006 |
| JP | 2009-250743 A | 10/2009 |
| JP | 2009-270940 A | 11/2009 |
| JP | 2010-256051 A | 11/2010 |
| JP | 2010-261823 A | 11/2010 |

* cited by examiner

AUTOMATIC ANALYZER AND REAGENT PROCESSING METHOD IN AUTOMATIC ANALYZER

TECHNICAL FIELD

The present invention relates to an automatic analyzer that analyzes biological samples such as blood and urine.

BACKGROUND ART

The automatic analyzer is a device that quantitatively measures a target test item by adding a reagent to a biological sample such as blood or urine to bring about a reaction. Since the reagent triggers a specific reaction for a given target item, if a user wishes to measure multiple test items, then multiple types of reagents are to be loaded, registered, and used with regard to the test items involved.

Generally, before starting analysis, the user loads and registers the reagents sufficient for the day's tests in the analyzer.

However, at institutions where there are a large number of tests to be performed, the reagents that can be loaded before the start of analysis may not be sufficient, and additional reagents may need to be loaded and registered. In such cases, it takes time before analysis is resumed if the analyzer is stopped every time a reagent is registered. The laboratory will be managed more efficiently if reagents can be additionally registered while the analyzer is continuously performing its analysis.

Some techniques aimed at such management involve supplementing reagent storage means for analysis purposes with reagent storage means for replenishment and reagent bottle transfer means. Information about the reagents stored in the two reagent storage means is managed in such a manner that reagent management tasks including reagent registration and replacement work are automated for higher efficiency (Patent Document 1).

There are also known techniques for allowing reagent bottles to be replaced without stopping pipetting or without causing other stoppages even as the analysis or other analyzer operation is underway (Patent Document 2).

PRIOR ART DOCUMENT

Patent Documents

Patent Document 1
JP-2006-337386-A
Patent Document 2
JP-H10-142230-A

SUMMARY OF THE INVENTION

Problem to be Solved by the Invention

However, even if reagent replacement work is made more efficient, with reagents additionally registered while the analyzer is performing the analysis operation, the registered reagents may not become usable on the spot. In many cases, preparations are needed to make the additionally registered reagents usable.

Specifically, the following preparations are needed:

For example, if they are new, reagents such as those for use in immunoassays contain magnetic microparticles that are settled at a bottom of reagent containers. The reagents thus need to be stirred sufficiently for content evenness before analysis.

During analysis, a reagent containing magnetic microparticles need only be stirred for several seconds; when newly added, the reagent needs to be stirred for about 30 seconds. This means that if the automatic analyzer has a new reagent input during the analysis operation and causes the newly input reagent to be stirred, the reagent mixing mechanism of the analyzer cannot perform the mixing operation for analysis purposes, and the analyzer must interrupt its analysis operation during that time.

Also, the reagents for use on the automatic analyzer generally need to be calibrated in advance.

For these reasons, the laboratory typically performs its preparation processes altogether before starting analysis as the preparations before routine measurement.

However, if the previously registered reagents have been exhausted, or if an unregistered reagent is desired to be used for a test item requiring urgent measurement, the new reagent may be required to be additionally registered halfway through the analysis. In that case, the techniques described in Patent Literature 1 or 2 may be used to perform the registration efficiently, but the fact remains that the preparations are still needed.

In the past, if there were other requests for analysis, the preparation processes could not be started until the analysis operation regarding the requested measurements was finished. While the analysis was underway, the additionally registered reagent could not be used.

For example, although the reagent mixing mechanism needs to be used to stir the magnetic microparticles, the mechanism is operating during analysis for other tests, so that the mechanism can only be used after the analyzing of these tests is completed.

An object of the present invention is to provide an automatic analyzer and a reagent processing method therein whereby preparations can be performed for the reagent used to measure a highly urgent test item even during analysis operation.

Means for Solving the Problem

The above object of the present invention is accomplished by the following configuration:

There is provided a reagent processing method in an automatic analyzer in which the priorities of reagent preparation reflecting the remaining volumes of reagents in reagent containers stored in a reagent storage unit are stored in a storage unit. Information about the reagents held in the reagent containers loaded into the reagent storage unit is read out. The priorities of reagent preparation reflecting at least the remaining volumes of the reagents in the reagent containers stored in the reagent storage unit are updated for each reagent and stored into the storage unit. On the basis of the priorities of reagent preparation stored in the storage unit regarding the reagents about which the information is read by a reagent information reading mechanism and which are held in the reagent containers loaded into the reagent storage unit, it is determined whether or not a reagent preparation mechanism is to perform reagent preparation in preference to a sample analysis operation. The reagent preparation mechanism then performs the preparation for the reagent loaded into the reagent storage unit.

Effect of the Invention

It is thus possible to provide an automatic analyzer and a reagent processing method therein whereby preparations can be performed for a reagent used to measure a highly urgent test item even during an analysis operation.

MODE FOR CARRYING OUT THE INVENTION

Figure 1:
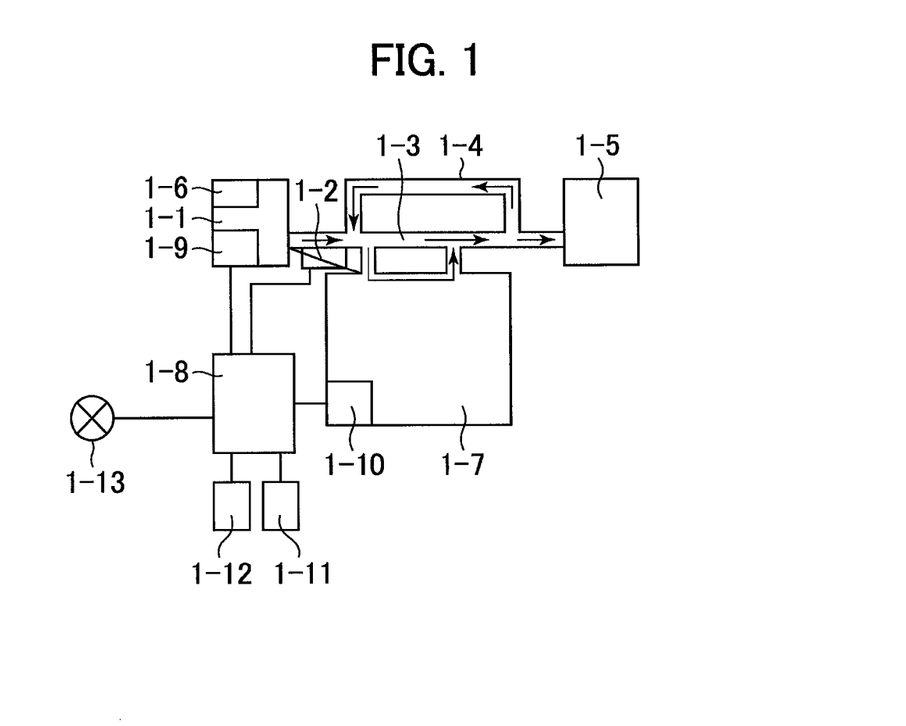
FIG. 1 is an overall configuration diagram of an automatic analyzer to which the present invention is applied.

Some embodiments of the present invention are explained below with reference to the accompanying drawings.
First Embodiment
First Embodiment FIG. 1 is an overall configuration diagram of an automatic analyzer to which the present invention is applied. In FIG. 1, the automatic analyzer includes a sample rack loading unit 1-1, an ID reading unit 1-2, a transfer line 1-3, a transfer line for rerun sample 1-4, an analytical module 1-7, a sample rack unloading unit 1-5, and a computer 1-8 for the whole system management.

The sample rack loading unit 1-1 is a unit that loads multiple sample racks. A calibrator storage unit 1-6 is a mechanism which stores reagents for use in calibration and which can load the calibrator automatically as requested. The analytical module 1-7 is located along and removably attached to the transfer line 1-3.

The analytical module 1-7 includes a computer 1-10 that performs control over the processes necessary in the analytical module 1-7. Also, a computer 1-9 controls the operations of the sample rack loading unit 1-1, transfer line 1-3, transfer line for rerun sample 1-4, and sample rack unloading unit 1-5.

The computers 1-9 and 1-10 and the ID reading unit 1-2 are connected to the computer 1-8 for the whole system management. The computer 1-8 is further connected with a control unit 1-12 through which necessary information is input, a display unit 1-11 that displays results of analyses, and an external network 1-13.

Figure 2:
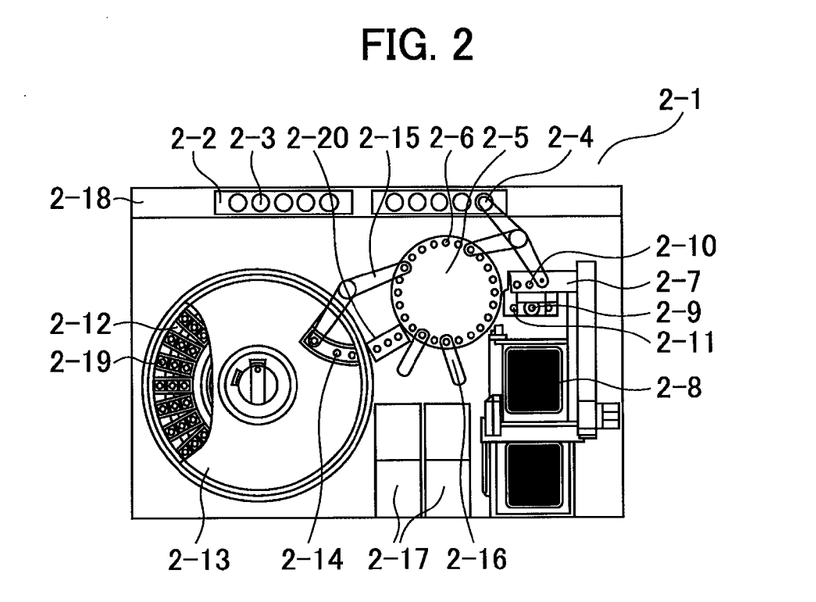
FIG. 2 is a schematic configuration diagram of an example of an analytical module shown in FIG. 1.

FIG. 2 is a schematic configuration diagram of an analytical module 2-1 as an example of the analytical module 1-7 shown in FIG. 1. With this embodiment of the present invention, an immunoassay analyzer for analyzing immunoassay test items is explained as an example of the analytical module 2-1.

In FIG. 2, sample containers 2-3 containing samples are placed on a transfer rack 2-2 of the analytical module 2-1. A rack transfer line 2-18 transports the transfer rack 2-2 to a sample pipetting position near a sample pipetting nozzle 2-4.

Multiple reaction cells 2-6 can be placed on an incubator disk 2-5. The incubator disk 2-5 can rotate to transport the circumferentially positioned reaction cells 2-6 to their predetermination positions.

A sample pipetting tip and reaction cell transfer mechanism 2-7 can be moved in three directions (X-, Y-, and Z-axes). The sample pipetting tip and reaction cell transfer mechanism 2-7 moves in predetermined ranges covering a sample pipetting tip and reaction cell storage component 2-8, a reaction cell mixing mechanism 2-9, a sample pipetting tip and reaction cell disposal opening 2-10, a sample pipetting tip attachment 2-11, and the incubator disk 2-5, when transferring the sample pipetting tips and reaction cells 2-6.

The sample pipetting tip and reaction cell storage component 2-8 has multiple unused reaction cells and sample pipetting tips. The sample pipetting tip and reaction cell transfer mechanism 2-7 moves to above the sample pipetting tip and reaction cell storage component 2-8, comes down to grab an unused reaction cell before moving up, moves on to a predetermined position above the incubator disk 2-5, and comes down to set the reaction cell.

The sample pipetting tip and reaction cell transfer mechanism 2-7 then moves to above the sample pipetting tip and reaction cell storage component 2-8, comes down to grab an unused sample pipetting tip before moving up, moves to above the sample pipetting tip attachment 2-11, and comes down to set the sample pipetting tip.

The sample pipetting nozzle 2-4 can turn and move vertically. After moving turnably to above the sample pipetting tip attachment 2-11, the sample pipetting nozzle 2-4 comes down to press-fit the sample pipetting tip onto an end of the sample pipetting nozzle 2-4. The sample pipetting nozzle 2-4 equipped with the sample pipetting tip moves to above the sample container 2-3 placed on the transfer rack 2-2, and comes down to aspirate a predetermined quantity of the sample held in the sample container 2-3.

After aspirating the sample, the sample pipetting nozzle 2-4 moves to above the incubator disk 2-5 and comes down to discharge the sample into the unused reaction cell 2-6 placed on the incubator disk 2-5. After discharging the sample, the sample pipetting nozzle 2-4 moves to above the sample pipetting tip and reaction cell disposal opening 2-10 and discards the used sample pipetting tip through the opening.

Multiple reagent containers 2-19 are placed on a reagent disk 2-12. Above the reagent disk 2-12 is a reagent disk cover 2-13 that keeps an inside of the reagent disk 2-12 at a predetermined temperature. A part of the reagent disk cover 2-13 is provided with a reagent disk cover opening 2-14.

A reagent pipetting nozzle 2-15 can rotate and move vertically. After moving rotatively to above the opening 2-14 of the reagent disk cover 2-13, the reagent pipetting nozzle 2-15 comes down, submerges an end of the nozzle into the reagent in a predetermined reagent container, and aspirates a predetermined amount of the reagent. The reagent pipetting nozzle 2-15 then goes up, moves rotatively to above a predetermined position of the incubator disk 2-5, and discharges the reagent into the reaction cell 2-6.

The reaction cell 2-6 into which the sample and the reagent were discharged is moved by the rotating incubator disk 2-5 to a predetermined position, before being transferred to the reaction cell mixing mechanism 2-9 by the sample pipetting tip and reaction cell transfer mechanism 2-7. The reaction cell mixing mechanism 2-9 gives a rotary motion to the reaction cell 2-6 to mix the sample and the reagent inside. After the mixing, the reaction cell is returned to the predetermined position on the incubator disk 2-5 by the sample pipetting tip and reaction cell transfer mechanism 2-7.

A reaction mixture aspirating nozzle 2-16 can rotate and move vertically. The reaction mixture aspirating nozzle 2-16 moves to above the reaction cell 2-6 in which the sample and the reagent were pipetted, mixed, and allowed to pass a predetermined reaction time on the incubator disk 2-5. The reaction mixture aspirating nozzle 2-16 then comes down to aspirate the reaction mixture from inside the reaction cell 2-6. The reaction mixture aspirated by the reaction mixture aspirating nozzle 2-16 is analyzed by a detection unit 2-17.

The reaction cell 2-6 from which the reaction mixture was aspirated is moved to a predetermined position by the rotating incubator disk 2-5. The reaction cell 2-6 is then moved by the sample pipetting tip and reaction cell transfer mechanism 2-7 from the incubator disk 2-6 to above the sample pipetting tip and reaction cell disposal opening 2-10, and discarded through the opening.

It should be noted that the present invention is not limited by the configuration of the above-described analytical module. This invention can be applied to mechanisms other than that of the analytical module above provided they have the reagent disk. For example, the reaction cells and sample pipetting tips need not be of disposable type; they can be washed for reuse. As another example, the equipment may be configured not to include the incubator, such as a general-purpose biochemical automatic analyzer.

Figure 3:
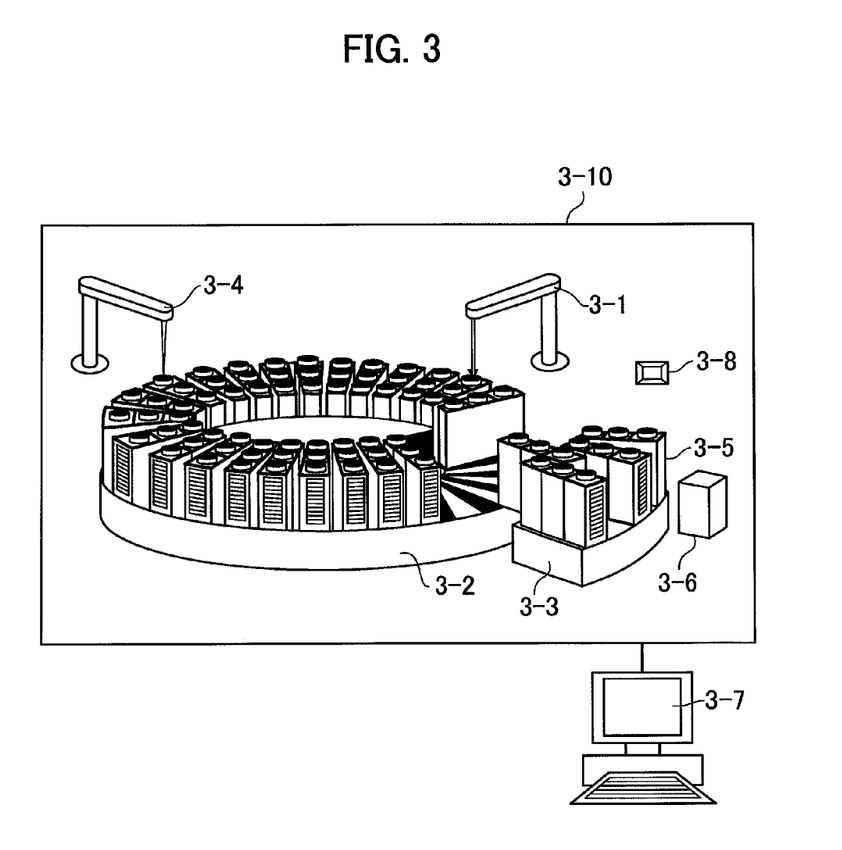
FIG. 3 is a configuration diagram of a reagent processing mechanism including components and equipment located near a reagent disk.

FIG. 3 is a configuration diagram of a reagent processing mechanism 3-10 including components and equipment located near the reagent disk 2-12 (indicated as a reagent disk 3-2 in FIG. 3).

In FIG. 3, reference character 3-1 stands for a reagent mixing mechanism, 3-2 for a rotary reagent loading mechanism, and 3-3 for a reagent loader. The reagent loading mechanism 3-2 and the reagent loader 3-3 carry reagent containers 3-5 (2-19). Each reagent container 3-5 contains a set of three liquid reagents necessary for measuring one test item. One of the three reagents in the reagent containers contains magnetic microparticles.

Reference character 3-6 denotes a reagent information reading mechanism and is positioned adjacent to the reagent loader 3-3. The reagent containers 3-5 bear reagent information. The reagent information reading mechanism 3-6 may be used to acquire the reagent information about the reagents placed on the reagent loader 3-3.

Reference character 3-8 represents a reagent loading/unloading button. Pressing the button 3-8 causes the reagent loader 3-3 to load or unload reagents to and from the reagent loading mechanism 3-2.

Further, reference character 3-4 (corresponding to 2-15) stands for a reagent pipetting nozzle, and 3-7 (corresponding to 1-10) denotes a control PC. The control PC 3-7 holds such information as the remaining volumes of the reagents loaded in the automatic analyzer, expiration dates of the reagents, their types, and their lots.

Figure 4:
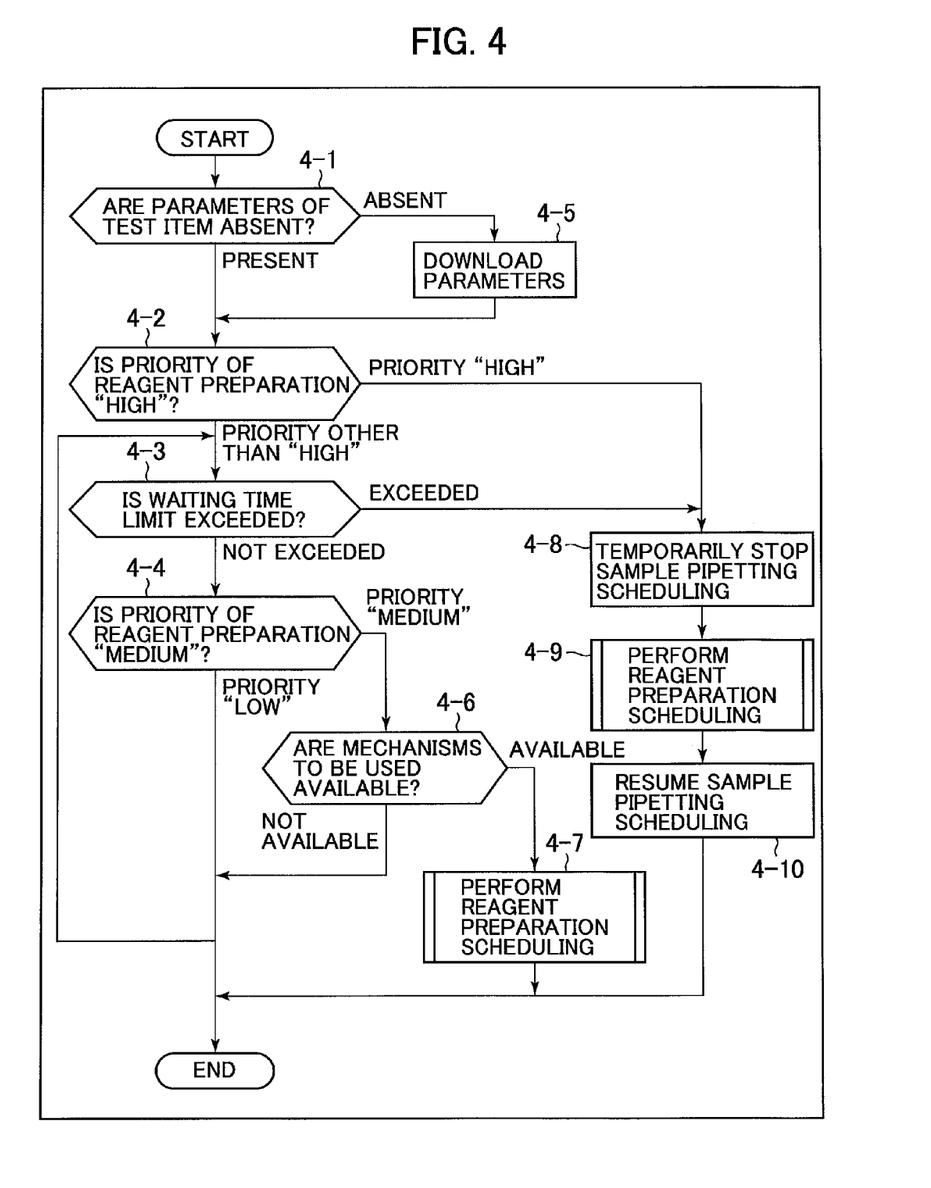
FIG. 4 is a flowchart for determining whether the reagent preparation of the present invention is to be performed preferentially.
Figure 5:
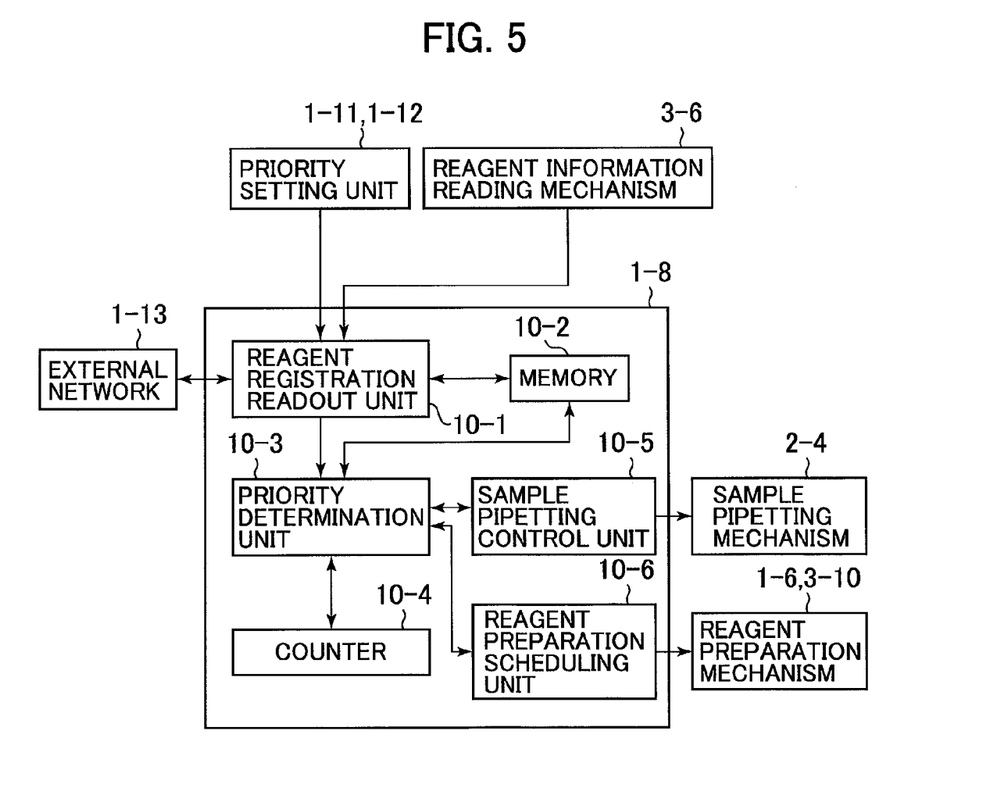
FIG. 5 is a functional block diagram of a computer for the whole system management for controlling the operations shown in the flowchart of FIG. 4.

FIG. 4 is a flowchart for determining whether reagent preparation is to be performed preferentially. FIG. 5 is a functional block diagram of the computer 1-8 for the whole system management for controlling the operations shown in the flowchart of FIG. 4. The computer 1-8 for the whole system management in FIG. 5 includes a reagent registration and readout unit 10-1, a memory 10-2, a priority determination unit 10-3, a counter 10-4, a sample pipetting control unit 10-5, and a reagent preparation scheduling unit 10-6. A priority setting unit (display unit 1-11 and control unit 1-12) transmits the priorities of reagents to the reagent registration readout unit 10-1. The reagent priorities thus transmitted are stored into the memory 10-2. For the registration of a new reagent, the reagent information read by the reagent reading mechanism 3-6 is stored into the memory 10-2 via the reagent registration readout unit 10-1.

In FIGS. 4 and 5, a new reagent is first placed in the reagent loader 3-3, and the reagent information read by the reagent information reading mechanism 3-6 is registered. In step 4-1, the reagent registration readout unit 10-1 determines whether there is any parameter of the analysis item for the reagent in question by referencing the data store in the memory 10-2. If it is determined that such parameters exist, step 4-2 is reached.

If it is determined in step 4-1 that no parameter exists, step 4-5 is reached. In step 4-5, the reagent registration readout unit 10-1 downloads the parameters of interest via the external network 1-13. The reagent registration readout unit 10-1 then goes to step 4-2.

In step 4-2, the priority determination unit 10-3 determines whether the priority of reagent preparation for the newly registered reagent is "high" on the basis of the data stored in the memory 10-2 before registration of the new reagent. If it is determined that the priority of the reagent preparation is "high," the priority determination unit 10-3 goes to step 4-8. In step 4-8, the priority determination unit 10-3 sends a command signal to the sample pipetting control unit 10-5 to temporarily stop a sample pipetting scheduling process. That is, the sample pipetting control unit 10-5 causes the sample pipetting mechanism 2-4 to temporarily stop its operation.

If it is determined in step 4-2 that the priority ofthe reagent preparation is not "high," step 4-3 is reached. In step 4-3, the priority determination unit 10-3 verifies the count on the counter 10-4 to determine whether or not a reagent preparation waiting time limit (set by the user) is exceeded. The waiting time has been counted since the reagent loader 3-3 loaded the reagent container containing the new reagent onto the reagent disk 3-2. If it is determined in step 4-3 that the reagent preparation waiting time limit is exceeded, then step 4-8 is reached.

In step 4-8, as described above, the sample pipetting scheduling process is stopped temporarily. Step 4-8 is followed by step 4-9. In step 4-9, the priority determination unit 10-3 sends a command signal to the reagent preparation scheduling unit 10-6. In turn, the reagent preparation scheduling unit 10-6 performs reagent preparation scheduling for the reagent preparation mechanism including the reagent processing mechanism 3-10 and calibrator storage unit 1-6 regarding the newly registered reagent. Step 4-9 is followed by step 4-10. In step 4-10, the priority determination unit 10-3 sends a command signal to the sample pipetting control unit 10-5 to resume sample pipetting scheduling.

If it is determined in step 4-3 that the waiting time limit is not exceeded, step 4-4 is reached. In step 4-4, the priority determination unit 10-3 verifies the priorities of reagent preparation stored in the memory 10-2. If it is determined that the priority of the verified reagent is "medium," step 4-6 is reached. In step 4-6, the priority determination unit 10-3 determines whether or not the mechanisms for reagent preparation are available via the sample pipetting control unit 10-5 and reagent preparation scheduling unit 10-6, i.e., whether or not reagent preparation can be performed anew.

If it is determined in step 4-6 that the mechanisms for reagent preparation are available, step 4-7 is reached. In step 4-7, the priority determination unit 10-3 sends a command signal to the reagent preparation scheduling unit 10-6, causing the latter to perform reagent preparation scheduling.

If it is determined in step 4-6 that the mechanisms for reagent preparation are not available, step 4-3 is reached again.

Also, if it is determined in step 4-4 that the priority of the reagent in question is "low," step 4-3 is reached again.

Figure 6:
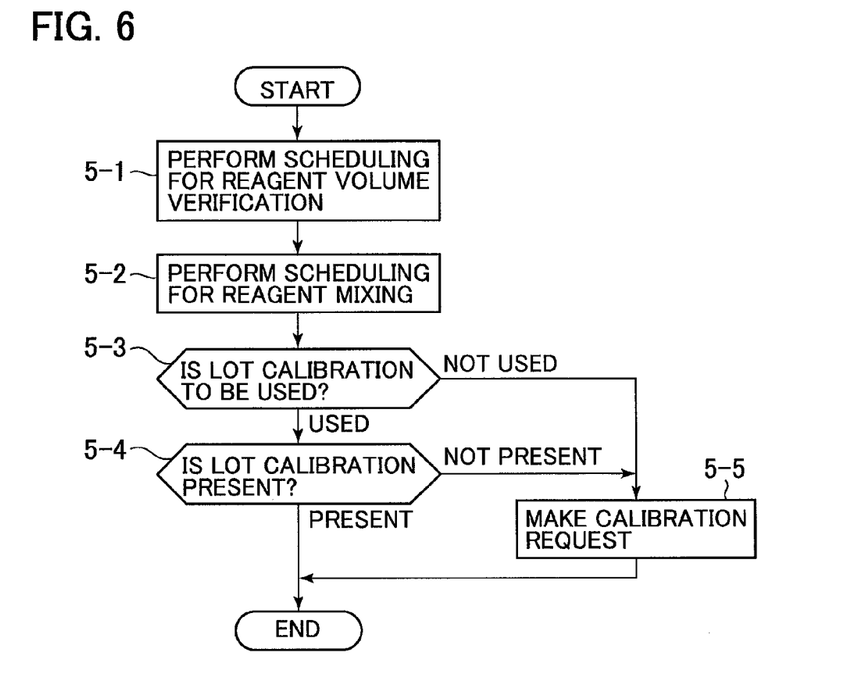
FIG. 6 is an operation flowchart for performing reagent preparation scheduling with a reagent preparation scheduling unit controlling the reagent processing mechanism.

FIG. 6 is an operation flowchart for performing reagent preparation scheduling with the reagent preparation scheduling unit 10-6 controlling the reagent processing mechanism (1-6, 3-10).

In FIG. 6, scheduling is performed first in step 5-1 to verify the volume of the loaded reagent. Next in step 5-2, scheduling for reagent mixing is performed.

In step 5-3, it is determined whether or not to use lot calibration. Lot calibration in this context means that when a reagent of the same type as that of a previously calibrated reagent and having the same lot number as the latter is loaded anew into the automatic analyzer, the previously measured calibration data is transferred to the newly loaded reagent.

If it is determined that lot calibration is not to be used, step 5-5 is reached. In step 5-5, a calibration request is made to the system, and the process is terminated.

If it is determined in step 5-3 that lot calibration is to be used, step 5-4 is reached. In step 5-4, it is determined whether lot calibration exists. If it is determined in step 5-4 that lot calibration does not exist, step 5-5 is reached. In step 5-5, a calibration request is made, and the process is terminated.

If it is determined in step 5-4 that lot calibration exists, then the process is terminated then and there.

Figure 7:
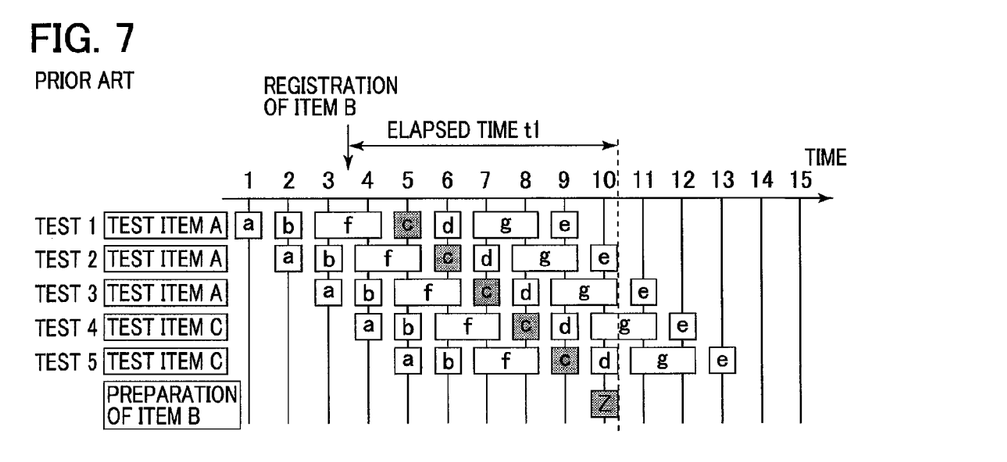
FIG. 7 is a diagram showing an elapsed time, with the present invention not applied, from the time a reagent whose priority is "high" is registered until the reagent preparation (magnetic microparticle intial mixing) is completed.
Figure 8:
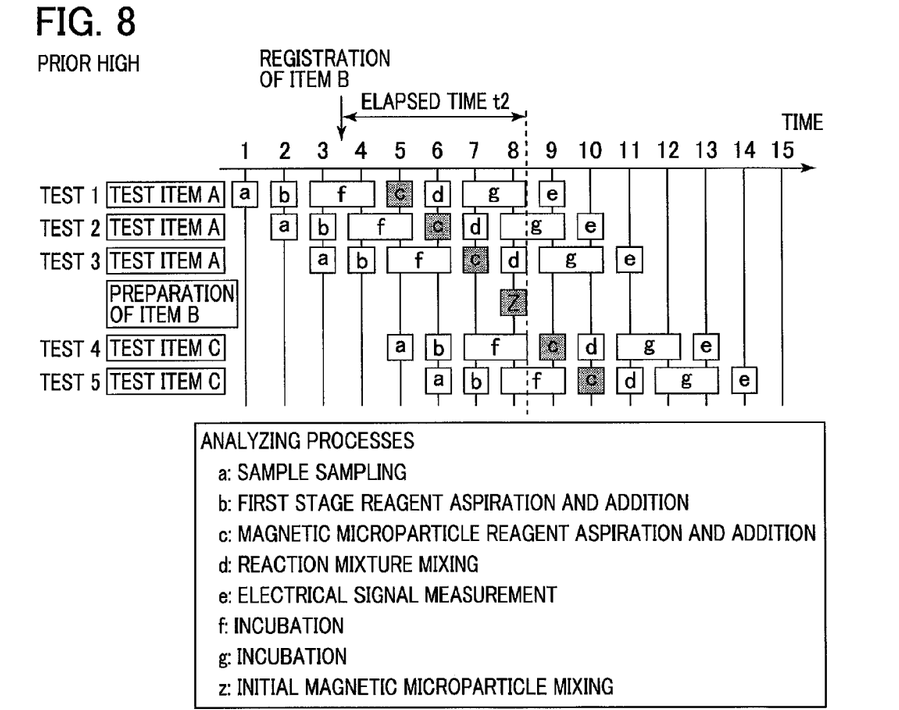
FIG. 8 is a diagram showing an elapsed time, with the present invention applied, from the time a reagent whose priority is "high" is registered until the reagent preparation (magnetic microparticle intial mixing) is completed.

FIGS. 7 and 8 are each a diagram showing an elapsed time from the time a reagent whose priority is "high" is registered until the reagent preparation (magnetic microparticle intial mixing) is completed. FIG. 7 gives an example in which the present invention is not applied, and FIG. 8 depicts an example in which the present invention is applied.

In each of the examples in FIGS. 7 and 8, five test items are requested. In reagent preparation and in analysis, the operation in which the mechanisms involved interfere with one another is "magnetic microparticle reagent aspiration and addition (c)." Where the reagent priority is high, magnetic microparticle intial mixing is scheduled with regard to item B after "test 3," which renders elapsed time t2 shorter than elapsed time t1 (t2<t1). That is, where the priority of the reagent in question is "high," applying the present invention makes it possible to complete the reagent preparation faster than if the invention is not applied.

Figure 9:
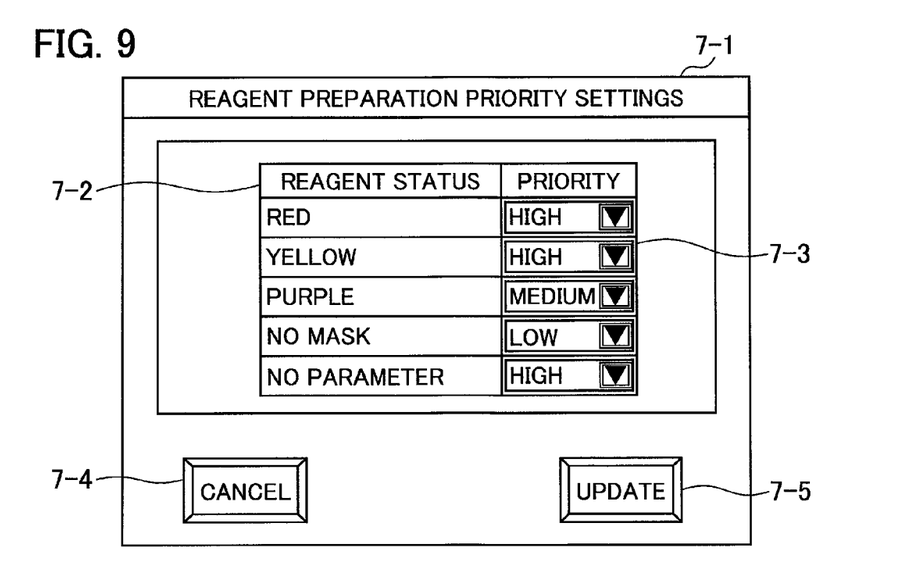
FIG. 9 is a diagram showing a typical screen for the setting of reagent preparation priorities.

FIG. 9 is a diagram showing a typical screen 7-1 for the setting of reagent preparation priorities, displayed on the display unit 1-11. Whereas this is an example of the screen on which reagent preparation priorities are to be set solely in terms of the remaining volumes of reagents, the priorities may be set alternatively by taking into account other elements such as the stability of the reagent during mixing.

In FIG. 9, reference character 7-2 stands for reagent status, 7-3 for combo boxes for selecting priorities, 7-4 for a cancel button, and 7-5 for an update button. On the basis of the conditions set through this screen, the priority of preparation for a given reagent is determined. Reagent status can be determined automatically by the reagent registration readout unit 10-1 of the automatic analyzer. Depending on the reagent status, the priority is changed automatically before being stored into the memory 10-2.

In the example of FIG. 9, the color red indicates that the reagent container is empty. The color yellow indicates that the reagent in the reagent container has decreased to a predetermined volume and that the reagent will not last for one day (e.g., the remaining volume will be exhausted in about a half day). In both cases, the priority is "high." The color purple indicates that the remaining volume of the reagent will be exhausted in one day and that the priority is "medium." Where there is no parameter, the priority of the reagent is "high"; where there is no mask (where the remaining volume will last for more than one day), the priority is "low." If an unregistered reagent of a new type is loaded, it is determined that the reagent in question has been exhausted so that the priority is "high."

Figure 10:
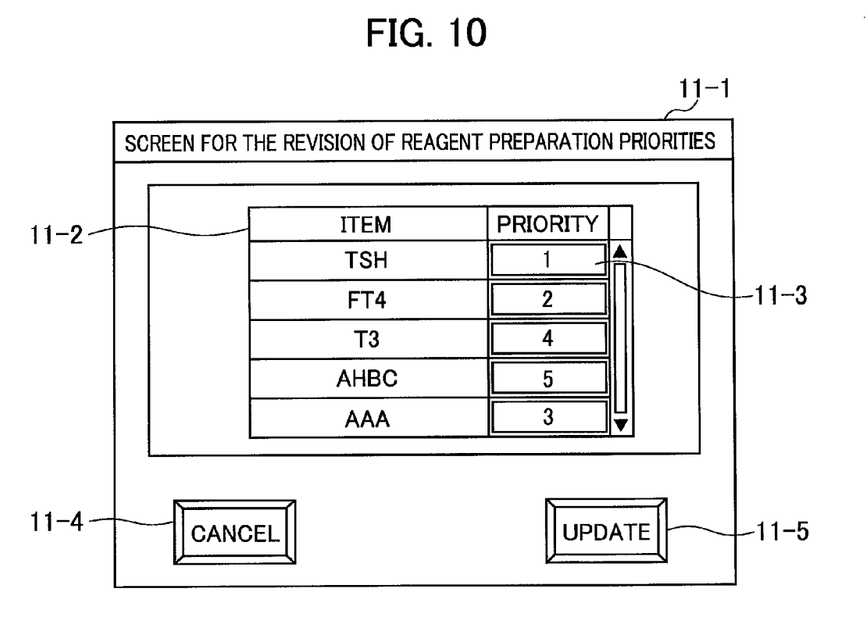
FIG. 10 is a diagram showing a typical screen for the revision of reagent preparation priorities.

FIG. 10 is a diagram showing a typical screen 11-1 for the revision of reagent preparation priorities, displayed on the display unit 1-11. In FIG. 10, the screen includes items 11-2, text boxes 11-3 for the revision of reagent preparation priorities, a cancel button 1-4, and an update button 11-5. This screen permits verification of the preparation priority regarding each reagent as stored in the memory 10-2, and revision of the priorities.

Figure 11:
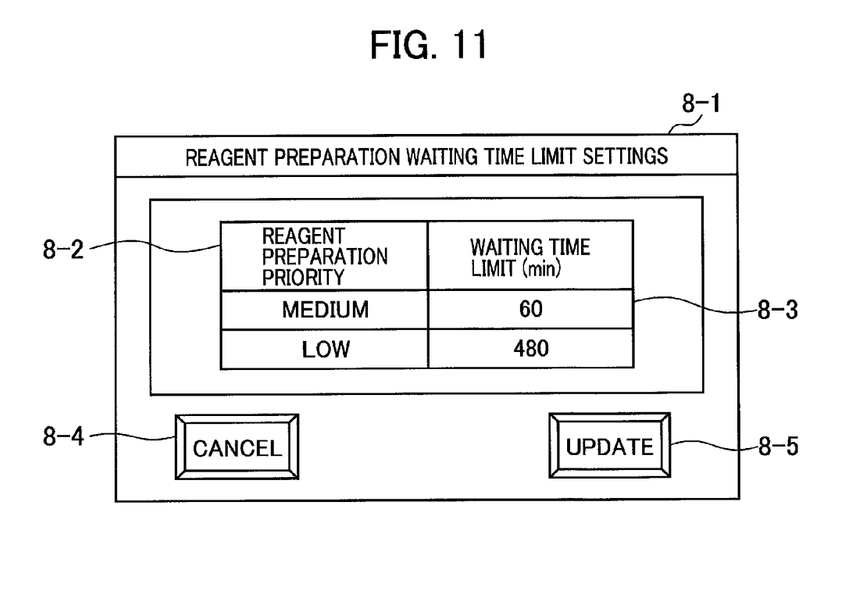
FIG. 11 is a diagram showing a typical screen for the limit setting of reagent preparation waiting time.

FIG. 11 is a diagram showing a typical screen 8-1 for the limit setting of reagent preparation waiting time, displayed on the display unit 1-11.

In FIG. 11, reference character 8-2 stands for reagent preparation priorities, 8-3 for text boxes in which to input waiting time limits (60 minutes for "medium" priority, 480 minutes for "low" priority), 8-4 for a cancel button, and 8-5 for an update button. On the basis of the conditions set through this screen, the waiting time limit for reagent preparation is determined.

Figure 12:
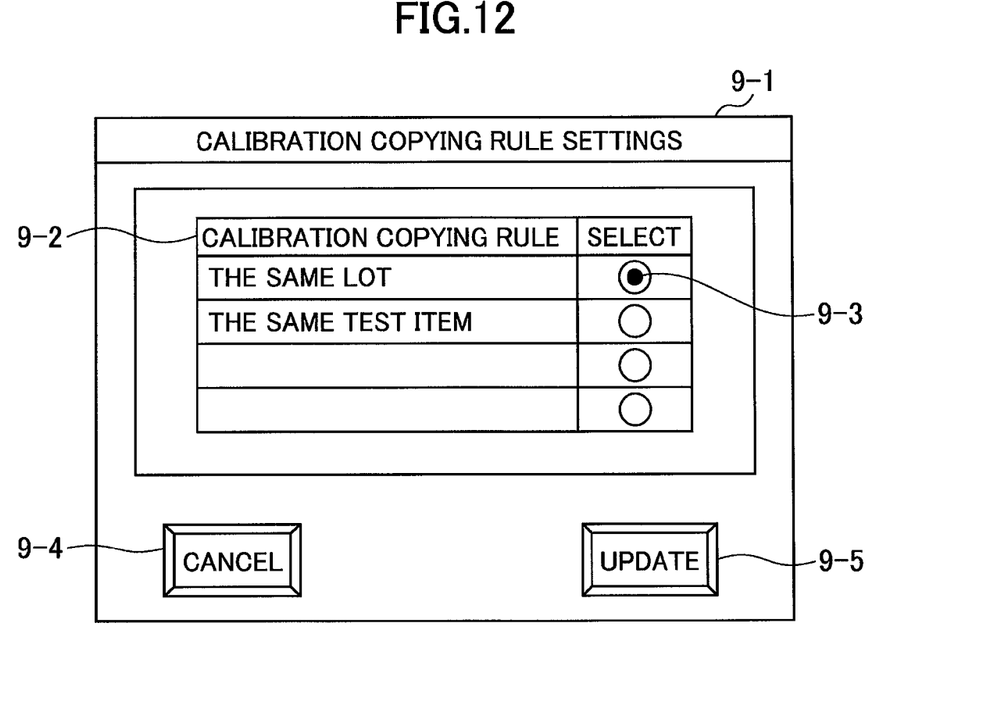
FIG. 12 is a typical setting screen for calibration copying rules.

FIG. 12 is a typical setting screen 9-1 for calibration copying rules, displayed on the display unit 1-11. In FIG. 12, reference character 9-2 stands for the calibration copying rules that can be selected, 9-3 for the radio buttons for selecting the rule, 9-4 for a cancel button, and 9-5 for an update button. On the basis of the rules set through this screen, it is determined whether or not the existing results of calibration are to be used.

If the rules have been set to permit the use of the existing results of calibration and if an analysis request has arrived requesting the use of a reagent for which the reagent preparation has yet to be performed by the reagent loading mechanism 3-2, the preparation for that reagent is given the highest priority so that the requested analysis can be performed.

According to the present invention described above, depending on the status of the reagents loaded in the automatic analyzer, the preparations for the loaded reagents are prioritized and their priorities are stored into the memory.

Specifically, an operation screen of the automatic analyzer is initially provided with a user interface through which the priorities of reagent preparation may be registered in accordance with the status of the reagents loaded in the automatic analyzer for the test items of interest. And according to the priorities thus established, the preparation for a given reagent may be performed to make the reagent actually usable for the measurement of interest in preference to the preparations for the reagents involved in other measurements.

The states in which a reagent is loaded regarding a test item include: a state where the remaining volume of the reagent is zero and the measurement is thus not available, a state where the measurement is available but the remaining volume of the reagent is insufficient, a state where the remaining volume of the reagent is enough to last for about one day, a state where the remaining volume of the reagent will last for more than one day, and a state where the parameters for using the reagent are not registered.

If, like the present invention, reagents are not prioritized, the preparation process for any reagent container that may be added during analysis needs to wait until after the requested analysis has been completed. The reason for this is that the pipetting and the mixing of a reagent are performed on the reagent container placed on the reagent disk and that the pipetting operation and the mixing operation cannot be performed simultaneously on any given reagent container.

With the present invention, the preparation for a loaded reagent is given "high," "medium," or "low" priority. If the priority is "high," the scheduled analysis is interrupted temporarily to have the preparation for the reagent scheduled for registration. If the priority is "medium," the preparation is scheduled into a time period in which the mechanisms necessary for the preparation are available so that the throughput of analysis will not drop. If the priority is "low," the preparation is scheduled when the number of reagent containers containing the same reagent has dropped to, say, three or less in the automatic analyzer.

In this manner, the preparations for the reagents of high urgency are preferentially performed automatically, while the preparations for the reagents of low urgency are not carried out so as to delay their degradation. This allows the automatic analyzer to be operated flexibly.

Thus according to the present invention, it is possible to provide an automatic analyzer and a reagent processing method therein whereby preparations can be performed for the reagent used to measure a highly urgent test item even during analysis operation.

Although the example in FIG. 5 is shown made up of functional blocks inside the computer 1-8 for the whole system management, the functional blocks 10-1 through 10-6 may also be constituted as electrical or electronic circuits separate from the computer 1-8 for the whole system management.

Second Embodiment

In another embodiment of the present invention, the reagent preparation priorities may be prioritized using a reagent loading/unloading button 3-8.

The operator presses the reagent loading/unloading button 3-8 when loading a reagent from the reagent loader onto the reagent disk. At this point, the manner of operating the reagent loading/unloading button 3-8 can determine the priority of the preparation for the reagent to be loaded.

For example, if the reagent loading/unloading button 3-8 is long pressed, the preparation for the reagent to be loaded is given "high" priority unconditionally. If the reagent loading/unloading button 3-8 is short pressed, the preparation for the reagent to be loaded may be determined in accordance with the conditions set beforehand by the user. According to this embodiment, the reagent containers containing the same type of reagent can be given different priorities flexibly depending on the status of analysis.

Even in the case above, the screen 11-1 for the revision of reagent preparation priorities may still be provided. This screen permits revision of the priorities depending on the circumstances so that, say, a reagent set for low priority when loaded but later desired to be used urgently can be given a new priority.

DESCRIPTION OF REFERENCE CHARACTERS 1-1 Sample rack loading unit
1-2 ID reading unit
1-3 Transfer line
1-4 Transfer line for rerun sample
1-5 Sample rack unloading unit
1-6 Calibrator storage unit
1-7 Analytical module
1-8 Computer for the whole system management
1-9 Computer for analytical module
1-10 Computer for analytical module
1-11 Display unit
1-12 Control unit
1-13 External network
2-1 Analyzer
2-2 Rack
2-3 Sample container
2-4 Sample pipetting nozzle
2-5 Incubator disk
2-6 Reaction cell
2-7 Sample pipetting tip and reaction cell transfer mechanism
2-8 Sample pipetting tip and reaction cell storage component
2-9 Reaction cell mixing mechanism
2-10 Sample pipetting tip and reaction cell disposal opening
2-11 Sample pipetting tip attachment
2-12 Reagent disk
2-13 Reagent disk cover
2-14 Reagent disk cover opening
2-15 Reagent pipetting nozzle
2-16 Reaction mixture aspirating nozzle
2-17 Detection unit
2-18 Rack transfer line
2-19 Reagent container
3-1 Magnetic microparticle mixing mechanism
3-2 Reagent loading mechanism
3-3 Reagent loader
3-4 Reagent pipetting mechanism
3-5 Reagent container
3-6 Reagent information reading mechanism
3-7 Control PC
3-8 Reagent loading/unloading button
7-1 Screen for the setting of reagent preparation priorities
7-2 Reagent status
7-3 Combo box for selecting priority
7-4 Cancel button
7-5 Update button
8-1 Screen for the limit setting of reagent preparation waiting time
8-2 Reagent preparation priority
8-3 Text box in which to input waiting time limit
8-4 Cancel button
8-5 Update button
9-1 Calibration transfer rules setting screen
9-2 Calibration transfer rules
9-3 Radio buttons for rule selection
9-4 Cancel button 9-5 Update button
10-1 Reagent registration readout unit
10-2 Memory
10-3 Priority determination unit
10-4 Counter
10-5 Sample pipetting control unit
10-6 Reagent preparation scheduling unit
11-1 Screen for the revision of reagent preparation priorities
11-2 Item
11-3 Text box for the revision of priority
11-4 Cancel button
11-5 Update button

The invention claimed is:

1. An automatic analyzing system comprising:
an automatic analyzer for analyzing samples, which comprises:
a reagent disk storing a plurality of reagent containers that respectively contain reagents;
a reagent mixer configured to mix reagents contained in the plurality of reagent containers stored in the reagent disk;
a sample pipetting nozzle configured to suction a sample and discharge the sample into a reaction vessel;
a reagent pipetting nozzle configured to suction a reagent from a reagent container of the plurality of reagent containers and discharge the reagent into a reaction vessel;
a detector configured to analyze a mixture of the discharged sample and the discharged reagent and perform a calibration measurement of a reagent;
a reagent loader configured to load one or more new reagent containers containing a reagent onto the reagent disk;
a reagent information reading mechanism configured to read information from the one or more new reagent containers; and
a system management computer connected to the automatic analyzer, which is programmed to:
control the automatic analyzer to continuously perform an analysis operation to analyze samples, which includes at least controlling the sample pipetting nozzle to suction a sample, controlling the reagent mixer to mix a reagent contained in a reagent container in the reagent disk for a first period of time, controlling the reagent pipetting nozzle to suction a reagent, and controlling the detector to measure a mixture of a discharged reagent and a discharged sample,
control the reagent information reading mechanism to read information from the one or more new reagent containers in the reagent loader that identifies the contained reagent,
store reagent information in association with identification information of a plurality of reagents, in a memory of the computer, that includes priority information, which indicates whether the analysis operation of the automatic analyzer is to be interrupted so that preparation processing of the reagent identified by the identification information is to be performed during the interruption,
judge, based on the priority information stored in association with the identification information that matches the information from the one or more new reagent containers in the reagent loader read by the reagent information reading mechanism that identifies the contained reagent, whether the analysis operation of the automatic analyzer should be interrupted for the reagent contained in the one or more new reagent containers in the reagent loader read by the reagent information reading mechanism to perform the reagent preparation process,
if the reagent preparation process is judged to be performed:
suspend suction of the sample by the sample pipetting nozzle thereby interrupting the analysis operation,
perform the reagent preparation processing, which includes at least one of controlling the reagent mixer to mix the reagent of the one or more new reagent containers for a second period of time, which is longer than the first period, and controlling the detector to perform a calibration measurement of the reagent, and
resume the sample suction by the sample pipetting nozzle after the reagent preparation processing is completed, thereby resuming the analysis operation.

2. The automatic analyzing system according to claim 1, wherein the stored reagent information for each reagent on the reagent disk includes information indicating a remaining volume of each of the reagents in the reagent containers stored in the reagent disk, and
wherein the priority information is based on the information indicating the remaining volumes of the reagent in the reagent container on the reagent disk that corresponds to the reagent contained in the one or more new reagent containers.

3. The automatic analyzing system according to claim 1, wherein the system management computer further comprises a display, and
wherein the system management computer is further programmed to: display a screen, on the display, for setting, a priority of whether the analysis operation of the automatic analyzer is to be interrupted for each of the reagents on the reagent disk based on the respective volumes of the reagents on the reagent disk, and receive an input for changing the priority.

4. The automatic analyzing system according to claim 3, wherein the analyzer further comprises a button located near the reagent loader, and
wherein the system management computer is further programmed to determine that reagent preparation processing is judged to be performed for the reagent of the one or more new reagent containers loaded by the reagent loader if the button is depressed for longer than a predetermined time.

5. The automatic analyzing system according to claim 1, wherein the system management computer is further programed to control the reagent mixer to mix the reagents during reagent preparation processing while at least the detector analyzes a mixture of a reagent and a sample during the analysis operation.

6. The automatic analyzing system according to claim 2, wherein the priority information is "high" if, the stored reagent information for the reagent stored on the reagent disk that corresponds to the reagent of the one or more new reagent containers indicates that the remaining volume of the reagent in the reagent container is less than a first threshold value,
wherein the priority information is "medium" if the remaining volume of the reagent in the reagent container is equal to or more than the first threshold value and equal to or less than a second threshold value, and
wherein the priority information is "low" if the remaining volume of the reagent in the reagent container is more than the second threshold value.

7. The automatic analyzing system according to claim 6, further comprising a counter which counts a time elapsed from a time when the one or more new reagent containers are loaded into the reagent disk,     wherein the system management computer is programmed to determine if the priority information for the reagent is "medium" or "low," whether or not the time counted by the counter has exceeded a predetermined waiting time limit, and issue a command if the counted time is determined to have exceeded the waiting time limit, the command causing the reagent preparation processing to begin. operation.

8. The automatic analyzing system according to claim 1, wherein the system management computer is further programmed to: determine that calibration for the reagent of the one or more new reagent containers is not necessary if the memory stores calibration information of a reagent for the same test item that corresponds to the reagent of the one or more new reagent containers, and if the corresponding reagent has been previously calibrated.

9. The automatic analyzing system according to claim 1, wherein the system management computer is further programmed to control the reagent loader to load one or more new reagent containers onto the reagent disk during the analysis operation.

\* \* \* \* \*